US010092023B2

(12) United States Patent
Dardelle et al.

(10) Patent No.: US 10,092,023 B2
(45) Date of Patent: Oct. 9, 2018

(54) HYBRID COACERVATE CAPSULES (71) Applicant: FIRMENICH SA, Geneva (CH)

(72) Inventors: Grégory Dardelle, Geneva (CH);
Pascal Beaussoubre, Geneva (CH);
Philipp Erni, Geneva (CH)

(73) Assignee: Firmenich SA, Geneva (CH)

( * ) Notice: Subject to any disclaimer, the term of this patent is extended or adjusted under 35 U.S.C. 154(b) by 347 days.

(21) Appl. No.: 14/402,469

(22) PCT Filed: May 23, 2013

(86) PCT No.: PCT/EP2013/060619
§ 371 (c)(1),
(2) Date: Nov. 20, 2014

(87) PCT Pub. No.: WO2013/174921
PCT Pub. Date: Nov. 28, 2013

(65) Prior Publication Data
US 2015/0104545 A1 Apr. 16, 2015

(30) Foreign Application Priority Data
May 24, 2012 (EP) .................................. 12169278

(51) Int. Cl.
A23L 2/00 (2006.01)
A23L 1/22 (2006.01)
A23L 2/56 (2006.01)
A61K 8/65 (2006.01)
A61K 8/73 (2006.01)
A61Q 19/00 (2006.01)
A61K 8/11 (2006.01)
A23P 10/30 (2016.01)
A23L 29/25 (2016.01)
A23L 29/281 (2016.01)
A23L 29/294 (2016.01)
A23L 27/00 (2016.01)
A23L 27/20 (2016.01)

(52) U.S. Cl.
CPC ............ *A23L 1/22016* (2013.01); *A23L 2/56* (2013.01); *A23L 27/203* (2016.08); *A23L 27/72* (2016.08); *A23L 29/25* (2016.08); *A23L 29/284* (2016.08); *A23L 29/294* (2016.08); *A23P 10/30* (2016.08); *A61K 8/11* (2013.01); *A61K 8/65* (2013.01); *A61K 8/73* (2013.01); *A61Q 19/00* (2013.01); *A23V 2002/00* (2013.01); *A61K 2800/10* (2013.01)

(58) Field of Classification Search
CPC ...... A23L 1/22016; A23L 2/56; A23L 27/203; A23L 27/72; A23L 29/25; A23L 29/284; A23L 29/294; A23P 10/30; A61K 8/11; A61K 8/65; A61K 8/73; A61K 2800/10; A61Q 19/00; A23V 2002/00
See application file for complete search history.

(56) References Cited

U.S. PATENT DOCUMENTS

| 3,627,581 | A | * | 12/1971 | Phillips, Jr. | .......... | B41M 5/1655 |
|---|---|---|---|---|---|---|
| | | | | | | 428/402.21 |
| 4,115,315 | A | | 9/1978 | Marinelli | | |
| 4,394,287 | A | | 7/1983 | Scarpelli | | |
| 4,428,869 | A | | 1/1984 | Munteanu et al. | | |
| 4,430,415 | A | * | 2/1984 | Aono | .................. | G03C 8/4013 |
| | | | | | | 430/138 |
| 5,603,952 | A | | 2/1997 | Tastemaker | | |
| 6,325,951 | B1 | | 12/2001 | Soper et al. | | |
| 6,969,530 | B1 | * | 11/2005 | Curtis | .................. | A61K 9/5057 |
| | | | | | | 264/4.1 |
| 7,794,836 | B2 | * | 9/2010 | Vasishtha | .................. | B01J 13/02 |
| | | | | | | 264/4.1 |
| 2012/0128978 | A1 | | 5/2012 | Ballweg et al. | | |

FOREIGN PATENT DOCUMENTS

| EP | 316054 A1 | 5/1989 |
|---|---|---|
| EP | 455598 A1 | 11/1991 |
| EP | 2150334 A1 | 2/2010 |
| FR | 1165805 A | 10/1958 |
| MX | 199704934 A | 6/1997 |
| WO | WO1996032017 A1 | 10/1996 |
| WO | WO2004008872 A2 | 1/2004 |
| WO | WO2004022220 A1 | 3/2004 |
| WO | WO2004022221 A1 | 3/2004 |
| WO | WO2005072228 A2 | 8/2005 |
| WO | WO2008142637 A1 | 11/2008 |
| WO | WO2009147119 A1 | 12/2009 |
| WO | WO2010070602 A2 | 6/2010 |
| WO | WO2010125094 A2 | 11/2010 |
| WO | WO2011124706 A1 | 10/2011 |
| WO | WO2012001604 A2 | 1/2012 |

OTHER PUBLICATIONS

International Search Report and Written Opinion, application PCT/EP2013/060619, dated Aug. 29, 2013.
de Kruif C.G., Weinbreck F., de Vries R., Current Opinion in Colloid & Interface Science, 9:340-349, 2004.

* cited by examiner

Primary Examiner — Irina S Zemel
(74) Attorney, Agent, or Firm — Winston & Strawn LLP (57) ABSTRACT The invention relates to a process for preparing a hybrid coacervate capsule by mixing a first polymer with particles to form particle/polymer complexes; interacting a second polymer with the particle/polymer complexes to form a mixture comprising hybrid complex coacervates which contain particulate inclusions; and adding a core material to the mixture so that the hybrid complex coacervates deposit as a coating layer around the core material. The capsules form another embodiment of the invention.

10 Claims, 5 Drawing Sheets

HYBRID COACERVATE CAPSULES

FIELD OF THE INVENTION

The invention relates to a method for preparing a delivery system such as a flavor or fragrance delivery system and the use of the delivery system for encapsulating a liquid, a solid, an emulsion or a dispersion containing a flavor or a fragrance.

BACKGROUND OF THE INVENTION

Coacervation is a liquid/liquid phase separation occurring in polyelectrolyte mixtures, resulting in the formation of two liquid phases: a polyelectrolyte-rich, so called coacervate phase, and a dilute continuous phase mostly devoid of polyelectrolyte. There are two types of coacervation, namely simple coacervation and complex coacervation, depending on whether the coacervate phase is constituted of a single polymer or of an ionic complex of two oppositely charged polymers. In the classical complex coacervation process used for encapsulation of active ingredients, the phase separation is induced such that the coacervate phase readily coats the drops or particles of the active ingredient. For encapsulation purposes, at least one of the polymers used should also be capable of forming a gel upon cooling. The process is conducted above the gelling temperature, and the temperature is reduced after coating the active ingredient (the core material) with complex coacervate phase, leading to temperature-induced gelation. Optionally, this procedure is followed by a hardening step during which the coacervate shell of the capsule is further cross-linked to provide a mechanically stable barrier shell. The classical coacervation process is described in a variety of publications, including WO 96/32017 (Tastemaker), FR 1,165,805 (The National Cash Register Company), MX 9,704,934 (Tastemaker Corporation), U.S. Pat. No. 6,325,951 (Givaudan), EP 0455598 (Warner-Lambert), EP 2150334 (Firmenich), and WO 2004/022221 (Firmenich).

Capsules with shells or matrices not exclusively made of polymers have also been disclosed. U.S. Pat. No. 4,394,287 discloses for example the use of water-insoluble additives such as perlescent materials, metal flakes, optical brighteners and UV absorbers incorporated into a polymer and coated at the surface of the microcapsule. This forms double layer types of capsules with a limited stability and also present a risk of delamination under certain stress conditions. U.S. Pat. No. 4,115,315 describes the use of perlescent particles embedded in the capsule wall. The purpose is to provide a visual effect only and the document is silent about any other functionality of the capsule. In terms of process, the particles are firstly added to the oil phase (internal phase material). The resultant dispersion is then added to an aqueous encapsulation media, during which the particles are said to flush out into the aqueous coacervate before proceeding to a milling and finally hardening. However with such a process, the migration of particles in the gel phase is limited. Consequently the particles are preferably concentrated at the oil/gel interface and not homogeneously distributed within the capsule wall. On the other hand, publication WO 2004/022220 A1 (Southwest Research Institute) relates generally to the preparation of core/shell microcapsules comprising a membrane that is made of a single polymer material and a structuring agent dispersed therein for protection of core materials with at least one oxygen-sensitive ingredient. The disclosure cites in very generic terms, different possible methods of microencapsulation in particular atomization, coacervation and co-extrusion. Although complex coacervation is cited as an option, only simple coacervation is obviously considered unless the structuring agent is added to the surface of the capsules. According to that teaching, the structuring agent can be added either after emulsion formation and/or by addition to the oil phase. Examples are shown to demonstrate the oxygen barrier properties and to describe the use of clay particles (kaolin) combined with a single polymer (gelatine) (simple coacervation) to obtain a membrane with enhanced barrier properties.

WO 2005/072228 A2 (E Ink) relates to the preparation of capsules, especially capsules intended for use in forming electrophoretic media through a coacervation process to better control the size distribution of core-shell capsules either by emulsifying a water-immiscible phase in a pre-formed coacervate of the protein (which in essence is a classical coacervation process) or by using a limited coalescence process with colloidal alumina as the surface-active particulate material, i.e., forming a solid-stabilized emulsion as a key step of the process.

WO 2009/147119 (Symrise) relates to a capsule with organic/inorganic hybrid wall. This publication describes synthetic polymer core/shell capsules, wherein the term "hybrid" refers to the presence of Si atoms in the silicon polymers synthesized. It does not disclose capsules containing inorganic (or other) particles included in the wall, and it is not related to coacervation methods.

WO 2010/125094 relates to the encapsulation of liquid or pasty active materials by extrusion through a nozzle, where the encapsulating material is described as a crosslinkable, at least partially condensated organically polymerizable, inorganic-organic hybrid material such as organopolysiloxanes. The term "hybrid" refers to the inorganic nature of Si atoms present in the organosilicon polymers used for a matrix encapsulation process.

WO 2011/124706 (BASF) relates to microcapsules having a core material encapsulated within a microcapsular shell useful for encapsulating flavor, perfume or fragrance, where the shell comprises at least one inorganic/hybrid material. Described therein is a process for preparing microcapsules in which a sol/gel precursor is mixed with a fragrance, perfume or flavor to form the oily core liquid, followed by emulsification of this oil to form an oil-in-water emulsion and subsequently undergoing a sol/gel process, resulting in capsules with a metal oxide or an inorganic/organic hybrid shell. This document discloses shell materials where polymeric or organic materials have been added to the shell or the capsule.

Despite these disclosures, there is a need for improved methods to make core-shell capsules having shells with desired mechanical properties, improved barrier properties for encapsulated material, and other desired functional properties. These methods are now provided by the present invention.

SUMMARY OF THE INVENTION

One embodiment of the present invention relates to a process for preparing a hybrid coacervate capsule. This process comprises mixing a solution of a first polymer with a dispersion of at least one type of solid particles at a temperature that is above the gelling temperature of the first polymer, wherein the first polymer adsorbs onto the at least one type of solid particles to produce a dispersion of particle/polymer complexes; adding a solution of a second polymer to the dispersion, wherein the second polymer interacts with the particle/polymer complexes to form hybrid complex coacervates containing particulate inclusions; adding a core material to the hybrid complex coacervates, wherein the hybrid complex coacervates deposit as a coating layer around the core material active/solution interface to form core/shell capsules each containing the core material encapsulated by a hybrid coacervate shell; and reducing the temperature of the core/shell capsules to a temperature that is below the gelling temperature of the first polymer. Optionally, but preferably, the process includes cross-linking of the hybrid coacervate shells of the capsules.

The solution of the first polymer is typically mixed with the dispersion of the at least one type of solid particles under conditions sufficient for the first polymer to adsorb readily onto the at least one type of solid particles, with the pH value and ionic strength of the solution of the first polymer being optimized for the formation of the particle/polymer complexes. Also, the hybrid coacervate has a suitable viscosity that allows the hybrid coacervate to deposit on the core material to form the capsule shell. Generally, the viscosity of the hybrid coacervate is between 100 mPas and 2,500,000 mPas at a temperature that is between 30° C. and 70° C., and at shear rates that is between 0.01/s and 100/s, and the hybrid coacervate contains at least one, and more preferably two or more, types of solid particles.

Another embodiment relates to a core/shell capsule produced according to the processes disclosed herein. The shell of the capsule contains at least one, and more preferably two or more, different types of solid particles which are generally selected from the group consisting of silicon oxides and other metal oxides, silicates, silver nanoparticles, magnesium and aluminum silicates (clays), sheet silicates (mica), diatomite, perlite, vermiculite, crystals of fats, fatty acids or fatty alcohols and mixtures thereof. In a preferred form, the capsule is transparent and has the appearance of glass beads, wherein the core is lighter than water but the capsule sediments under gravity or in centrifugal fields. Also, the core may include a solid active ingredient and/or a liquid active ingredient, with the latter typically being an oil.

The capsule thus comprises a core and a shell, wherein the shell is a hybrid coacervate material comprised of two coacervated polymers and at least one type of solid particles; and the core comprises a solid active ingredient and/or a liquid active ingredient of an oil.

DETAILED DESCRIPTION OF THE PREFERRED EMBODIMENTS

The invention provides a novel method of manufacturing core/shell capsules having shells with a significant amount of particulate inclusions. These shell compositions provide unexpected benefits to the core/shell capsules of the invention, such as desired mechanical properties; tuned shell density of the capsule; improved processability and facilitated drying of capsule; improved barrier properties for encapsulated material; reduced water content in the shell and desired functional properties, including but not limited to optical properties such as colour, opacity and iridescence; protection of the active (e.g. radiation absorbers to protect from UV); delivery (e.g. secondary encapsulation of a solid active or "co-active" in the shell); delivery and protection of the secondary active in the shell; masking (e.g., shell contains malodour capturing particles and core contains a fragrance); and nutritional/health benefit (e.g., iron).

For the purpose of the present invention, the term "hybrid coacervate capsule" means a core/shell capsule where the coating shell of the capsule is produced by three-component complex coacervation involving two polymers and at least one type of solid particles. In contrast, the term "classical coacervate capsule" refers to a core/shell capsule made by classical complex coacervation, a well-known and established encapsulation process that has long been used for inks, flavors, fragrances and other active ingredients.

Core Material of the Capsule

The core material of the hybrid coacervate capsule may be a liquid or solid hydrophobic material. Such hydrophobic materials are generally immiscible with water, and form a separate phase when mixed with water.

Preferably, the hydrophobic material is a hydrophobic liquid at room temperature, which is fully or partially immiscible with water so that it can be dispersed in the form of discrete emulsion drops within an aqueous phase during the manufacturing of the capsules. This requirement typically implies that the interfacial tension of the liquid active ingredient against water is at least 0.0001 N/m, and preferably at least 0.001 N/m. Furthermore, the hydrophobic material preferably contains at least one component for which the value of the base-ten logarithm of the partition coefficient between octanol and water (log P) is above 4. Nevertheless; the hydrophobic material may also contain additional components with log P<4.

For the purpose of the present invention, the term "hydrophobic material" also includes materials that remain solid at the temperatures of the process described herein. Preferably, such solid hydrophobic materials also form a separate phase with water when heated above their melting point.

Preferred hydrophobic materials for the core of the capsule include flavors, fragrances, pigments, dyes, sweeteners, cooling agents or other ingredients with organoleptic activity, nutritional ingredients, dietary supplements, therapeutic agents, drugs, or other bioactive agents.

Flavors and fragrances are particularly preferred for the purpose of the present invention. For the purpose of the present invention, the terms "flavors" and "fragrances" include a variety of flavor and fragrance materials of both natural and synthetic origin, including single compounds and mixtures thereof.

Specific examples of such ingredients may be found in the current literature, e.g. in Fenaroli's Handbook of Flavor Ingredients, 1975, CRC Press; Synthetic Food Adjuncts, 1947 by M. B. Jacobs, edited by Van Nostrand; or in Perfume and Flavor Chemicals by S. Arctander 1969, Montclair, N.J. (USA). These substances are well known to the person skilled in the art of perfuming, flavoring and/or aromatizing consumer products, i.e. of imparting or modifying the odor, flavor or taste of a consumer product traditionally perfumed, respectively flavored. More recent versions of such textbooks also describe many examples of suitable perfuming and/or flavoring ingredients and their mixtures.

The prior art and in particular the patent literature in the flavor and fragrance field is also rich in such citations.

Natural extracts can also be encapsulated into the system of the invention, including e.g. citrus extracts such as lemon, orange, lime, grapefruit or mandarin oils, or coffee, tea, mint, cocoa, vanilla oils or essential oils of herbs or spices, amongst other.

Preferably, ingredients with organoleptic activity also include capsaicin, cooling agents, and nutritional ingredients.

According to a particular embodiment, the core further includes solid particles such as that described below, dispersed therein.

Shell/Membrane of the Capsule

In preferred embodiments of the invention, the shell/membrane of the hybrid coacervate capsule of the invention comprises two coacervated polymers, a first polymer ("polymer 1") and a second polymer ("polymer 2"), and at least one type of solid particles. The at least one type solid particles provides the desired benefits, such as reduction of the amount of water in the membrane and other functional properties, to the hybrid coacervate capsule. The first polymer, polymer 1, is selected based on its ability to interact with the solid particles to form a first particle/polymer complex that is positively or negatively charged. The second polymer, polymer 2, then interacts with the first polymer/particle complex to induce a phase separation. The coacervate hybrid assembly is specially designed so that it is able to deposit at the surface of the active to encapsulate the latter. This deposition results in a core/shell capsule comprising a shell that contains solid inclusions entrapped in a polymeric gel matrix.

The polymers can be, for example, proteins, polysaccharides and polyacids that are generally known to be suitable for complex coacervation methods.

In some preferred embodiments, the first polymer, polymer 1, is a protein or a polypeptide capable of adsorbing at the surface of the particles to form a new complex that is positively or negatively charged. Proteins suitable for coacervation processes are gelatins and albumins or globulins from vegetable, animal or microbial sources. Typical molecular weights of proteins useful for the hybrid coacervation process are in the order of 40 KD to 500 KD, preferably from 15 KD to 250 KD. In one embodiment, the protein is present as an aggregator or oligomer so that the molecular weight is much greater. Suitable proteins include gelatins, whey proteins (such as lactoglobulin), pea proteins, potato proteins, or egg albumins (e.g. ovalbumin), caseins and caseinates.

In a preferred embodiment, the first polymer, polymer 1, is a protein, the solution of which forms a gel upon cooling. For the purpose of the present invention, the gelling temperature of the first polymer, polymer 1, is considered to be the relevant gelling temperature for the hybrid coacervate system.

In one preferred embodiment, the first polymer, polymer 1, is a gelatin. Suitable gelatins may be derived from a variety of sources, such as pork, beef, poultry or fish sources. Gelling temperatures of such gelatins are typically in the range of 29° C.-36° C. For a specific gelatin the gelling temperature should be measured by oscillatory rheometry using established laboratory methods. For the gelatins used here, the gelling temperature is determined on gelatin solutions using a Physica MCR300 rheometer (Anton Paar GmbH, Germany) equipped with parallel plate measuring geometry (disk diameter 50 mm, gap 0.75 mm), programmed to perform a temperature sweep experiment from a temperature of 60° C. to a temperature of 15° C. with a temperature ramp of −1° C./min at a controlled deformation amplitude of 2% and an oscillation frequency of 1 rad/s.

In one preferred embodiment of the invention, the first polymer, polymer 1, is positively charged for pH<8, resulting in low viscosity solutions in water at a temperature greater than the melting point of the considered polymer gel, and more preferably at T>30° C., and highly viscous solutions in water at room temperature. In one preferred embodiment, the first polymer, polymer 1, is gelatin.

In some preferred embodiment, the second polymer, polymer 2, is a non-protein polymer charged oppositely to the protein of the first polymer, polymer 1, in the range of pH values that are known to be of interest for coacervation. These non-protein polymers include gum arabic (also known as Acacia gum or gum acacia) and similar plant gums, gum tragacanth, CARBOPOL® poly(acrylic acid), low methoxy pectin, xanthan gum, sodium carboxymethyl guar gum, guar gum, high methoxyl pectin, carboxymethyl cellulose (CMC), alginates, carrageenans (including kappa-carrageenan, iota-carrageenan, lambda-carrageenan and mixtures thereof), dextrane sulfate, polyphosphates (e.g., sodium hexametaphosphates), or microbial exopolysaccharides. Details on the characteristics of suitable polymers can be found in the scientific literature on coacervation and on polyelectrolyte complexes (for example, in de Kruif C. G., Weinbreck F., de Vries R., Current Opinion in Colloid & Interface Science 9:340-349, 2004).

Preferably, the second polymer, polymer 2, is chosen among the group of weakly anionic polyelectrolytes including gum arabic and similar plant gums, carboxymethyl cellulose, low methoxy pectin, carbopol, sodium carboxymethyl guar gum, and alginates.

Most preferably, the second polymer, polymer 2, is negatively charged when the pH is greater than 2. In one preferred embodiment, the second polymer, polymer 2, is gum arabic.

The solid particles included in the hybrid coacervate shell represent a novel feature of the invention. These particles provide benefits including, but not limited to, an improvement of the barrier properties of the shell, a change in the capsule density, a reduction of the amount of water in the shell, and other benefits relevant for a specific functionality of the capsule such as nutritive value of the solid particles, desirable visual properties, screening from radiation, and responsiveness in a magnetic field to move or separate the capsules.

The solid particles include, but are not limited to, the groups of inorganic particles such as clays; organic particles such as latexes, starches, microcrystalline cellulose, cyclodextrin and mixtures thereof; composite nano- or microparticles such as porous particles containing a secondary active ingredient; particles carrying immobilized enzymes; nano/macro-fiber; and nano/macro-tube. In particular, the solid particles may be silicon oxides, such as silica (e.g., colloidal silica, such as that sold under the tradename KLEBOSOL® by AZ Electronic Materials, or fumed silica, available for example under the trade name AEROSIL® from Evonik) or silicates (e.g., synthetic silicate such as that sold under the tradename LAPONITE® by Rockwood Additives); other metal oxides such as iron oxide, aluminium oxide, titanium oxide; metal salts and their derivatives; hydroxides, salts of inorganic or organic acids and their mixtures (e.g., $TiO_2$, $FeO$, $Fe(OH)_2$, $FeCO_3$, $MgO$, $Mg(OH)_2$, $MgCO_3$, $Mg_3(PO_4)_2$, $CaCO_3$, $CaSO_4$, $Ca_5(PO_4)_3(OH)$, $Ca_3(C_6H_5O_7)_2$); silver nanoparticles; magnesium and aluminium silicates (clays); sheet silicates (mica); diatomite; perlite; vermiculite; polymer latexes; dietary fibers such as microcrystalline cellulose; lignin and chitin; cells (e.g., yeast cells) or fragments thereof; humic acid; enteric polymers (e.g., EUDRAGIT® FS 30 D and EUDRAGIT® L 100-55 from Evonik); crystals of fats, fatty acids or fatty alcohols, and mixtures thereof.

In one preferred embodiment, solid particle types include silicon oxides and other metal oxides, silicates, silver nanoparticles, magnesium and aluminium silicates (clays), sheet silicates (mica), diatomite, perlite, vermiculite, crystals of fats, fatty acids or fatty alcohols, and mixtures thereof.

In one preferred embodiment of the invention, the solid particles are negatively charged when the pH is greater than 2.

In one embodiment of the invention, the first polymer, polymer 1, adsorbs at the surface of the solid particles to form a new positively charged polymer/particle complex at pH>2. The coverage of particles by the first polymer, polymer 1, is preferably at least of 0.1 molecules of polymer 1 per $nm^2$ of particle surface.

In one embodiment of the invention, particles are smaller than 10 micrometers in at least one dimension.

In any one embodiment of the invention it is preferred that the dry matter composition of the hybrid coacervate shell is such that the ratio of the total mass of solid particles to the total mass of polymers 1 and 2 is between 0.01 and 1.85.

Cross-Linking Agents

After the formation of the hybrid coacervate shell, the shell is typically hardened using a cross-linking agent. Suitable agents for cross-linking include, but are not limited to, formaldehyde, acetaldehyde, glutaraldehyde, glyoxal, chrome alum, and transglutaminase. The enzyme transglutaminase, which is readily available commercially (e.g., from Ajinomoto Corp., Japan), is preferably used at 10-100 activity units per gram of the first polymer, for example, gelatin, and most preferably at 30-60 activity units per gram of the first polymer.

Preparation Method

The invention provides a process for preparing hybrid coacervate capsules of the invention, which process comprises the steps of:
(1) mixing a solution of a first polymer (solution A) with a dispersion of at least one type of solid particles (dispersion C), at a temperature that is above the gelling temperature of the first polymer, thereby adsorbing the first polymer onto the at least one type of solid particles to form a dispersion of particle/polymer complexes;
(2) adding a solution of a second polymer (solution B) to the dispersion of particle/polymer complexes formed in step (1) to interact with the particle/polymer complexes, thereby forming hybrid complex coacervates containing particulate inclusions;
(3) adding a core material (D) to the hybrid complex coacervates formed in step (2), which deposit as a coating layer around the core material active/solution interface to form core/shell capsules with a hybrid coacervate shell,
(4) reducing the temperature of the core/shell capsules to below the gelling temperature of the first polymer, and, optionally,
(5) hardening the hybrid coacervate shell of the capsules by cross-linking the protein fraction of the hybrid coacervate shell.

In a preferred embodiment of the invention, step (1) is performed under conditions sufficient for the first polymer to readily adsorb onto the solid particles. Preferably, step (1) is performed by adjusting the pH value and/or ionic strength of solution A to optimize the formation of particle/polymer complexes.

The sequence of steps (1) to (5) is an essential characteristic of the present invention. Following previously described processes to include particles in the shell of a capsule in the case of capsule membranes formed by complex coacervation of two polymers and particles would not allow to the same result. In particular, WO 2004/022220 A1 (Southwest Research Institute) teaches that particles may simply be added at any point during the process. This approach, which teaches to ignores steps (1) and (2) of the present invention's method, results in failure of encapsulation since a hybrid complex coacervate containing particles can only be formed if a proper dispersion of polymer 1/particle complexes is formed.

Tuning of Capsule Shell Density

The density of the hybrid coacervate capsules is easily controlled by modifying the amount of particulate inclusions in the shell/membrane. In contrast to standard capsules having the same size and containing the same core material as the hybrid coacervated capsules of the invention but made by classical coacervation which always float, the hybrid coacervate capsules of the invention can be engineered to either float or sediment, by including different amounts of particles (see FIG. 3).

Improvement of Barrier Properties for Encapsulated Material

The inclusion of solid particles in the shell/membrane of the hybrid capsules makes it possible to improve the barrier properties and to reduce the permeation of the active ingredient through the shell. Preparing capsules with a hybrid coacervate shell with solid particles according to the invention allows the formation of a more densely packed polymer/inorganic particle shell. This is especially pronounced upon removal of the water from the membrane upon drying of the capsules.

Hybrid Coacervate Capsules with Desired Functional Properties

By choosing solid particles with specific functional properties, hybrid capsules with desired function properties can be prepared. For example, this can be achieved by choosing particles with desired optical properties (such as color; opacity; iridescence), desired protective properties (such as using radiation absorbers to protect the active core ingredient from ultraviolet radiation), and nutritional/health benefits (with particles such as iron oxide or minerals).

The hybrid coacervate capsules produced using the method of the invention have multiple usages. For example, they can be used in food and beverages where capsules made by coacervation are commonly used, including, but not limited to, meat products, baked goods, cereal products, confectionary products including chewing-gums, preserves and spreads, dairy products such as yoghurts and other fermented milk products, milk drinks, and cheese products, frozen savory foods such as pizzas, meat preparations, and sandwiches, frozen sweet goods such as ice creams, sorbets and frozen yoghurts, and oral care products such as toothpastes, gels and mouthwashes.

The hybrid coacervate capsules of the invention can also be used in perfumery applications where capsules made by coacervation can be used, including, but not limited to, body wash products such as shower gels and soaps, body care products such as body creams and lotions, and air care or fine fragrance products. The hybrid coacervate capsules of the invention can also be used in products such as sunscreen lotions, deodorants and antiperspirant products.

EXAMPLES

The following examples are provided as illustrations of the preferred embodiments of the invention and are not intended to limit the scope of the invention.

Example 1

Preparation of Hybrid Coacervate Capsules with Shells Composed of Gelatin, Gum Arabic and Kaolin Particles Aqueous solutions of 10% wt. pork gelatine (A), 10% wt. gum arabic (B), an aqueous dispersion of 10% wt. kaolin particles (C) and limonene oil (D) are prepared separately and maintained at 50° C. in a water bath. In a beaker at 50° C., 15 g of the solution (A) are added to 35 g of warm demineralized water under mechanical shear. The pH of the solution is adjusted to 8.5 using NaOH 1M, before adding 40 g of the dispersion (C), and reducing the pH to 4.5 with HCl 1M. 10 g of solution (B) are then added to the mixture, followed by the addition of 10 g of the oil (D). Mechanical shear is maintained while the solution is allowed to cool down at room temperature. The result is a suspension of core-shell capsules which sediment at the bottom of the beaker, i.e., with a density different from the capsules prepared without particles, and exhibiting an opaque appearance with a white color. Thermogravimetric analysis of the residual solvent showed that no polymer and no particles were left in the solvent after this process.

The density of the whole capsule can be easily controlled by modifying the amount of particulate inclusions in the membrane. Comparing standard capsules with shells made by classical coacervation with hybrid coacervate capsules (both samples having the same sizes and containing the same core material), reveals that the hybrid coacervate capsules can be engineered to either float or sediment, depending on the composition of the hybrid coacervate shell.

Figure 3:
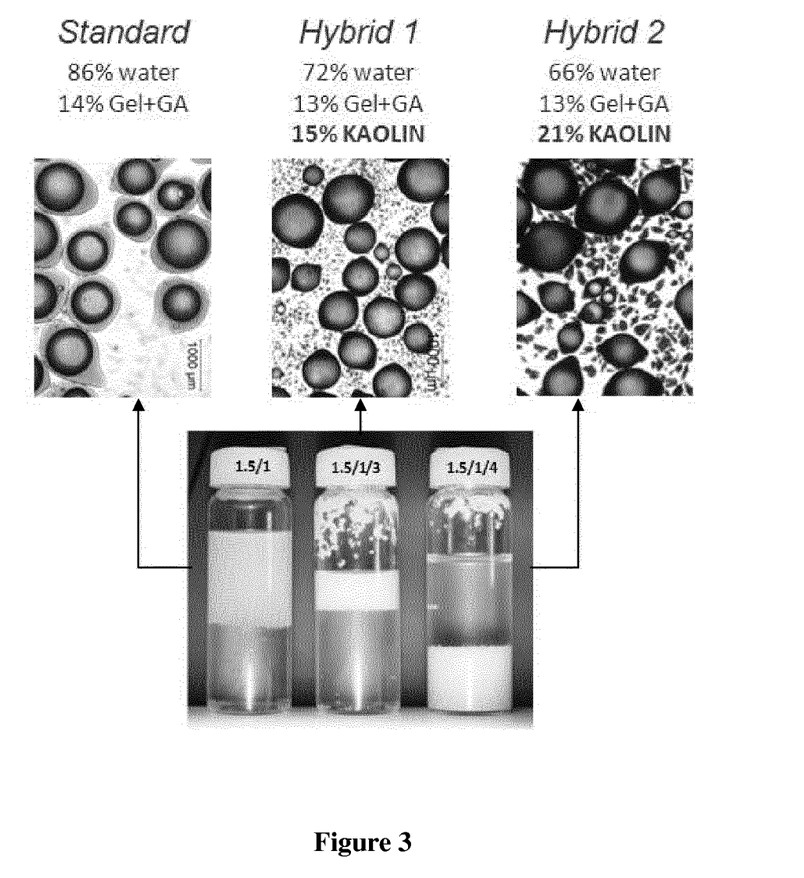
FIG. 3 shows microscope images of classical coacervate capsules (Standard) in comparison with hybrid coacervate capsules with two different shell compositions of gelatin/gum arabic/kaolin (Hybrid 1 and Hybrid 2). The figure also shows the effect of the shell composition of Hybrid 1 and Hybrid 2 on the relative density of all the capsules in a slurry: capsules with Hybrid 1 shells rise to the top of the sample bottle, whereas capsules with Hybrid 2 shells sediment to the bottom of the bottle.

Compositions of the shell capsules for standard and two different types of hybrid capsules are shown in the Table below. As shown in FIG. 3, the density of the capsules having hybrid coacervate shells can be modified by changing the amount of the inorganic kaolin particles included in the shell.

| | Dry matter composition of the shell Measured by Thermo Gravimetric Analysis | |
|---|---|---|
| | Polymer 1 + Polymer 2 (% w/w) | Particle inclusions (% w/w) |
| Standard | 100.0% | 0.0% |
| Hybrid 1 | 47.5% | 52.5% |
| Hybrid 2 | 40.2% | 59.8% |

Example 2

Preparation of Hybrid Coacervate Capsules with Shells Composed of Gelatin, Gum Arabic and Silica Particles Aqueous solutions of 10% wt. pork gelatine (A), 10% wt. gum arabic (B), an aqueous dispersions of 10% wt. silica particles (KLEBOSOL®30V25 obtained from AZ Electronics Materials) (C) and limonene oil (D) are prepared separately and maintained at 50° C. in a water bath. In a beaker at 50° C., 15 g of solution (A) are added to 70 g of warm demineralized water under mechanical shear. The pH is adjusted to 8.5 using NaOH 1M before adding 5 g of solution (C), and reducing the pH to 4.5 with HCl 1M. 10 g of solution (B) are then added to the mixture, followed by the addition of 10 g of (D). Mechanical shear is maintained while the solution is allowed to cool down at room temperature. The result is a suspension of core-shell capsules easier to dry, as compared to the standard capsules that do not contain particles, and displaying a different release of the encapsulated material when dried, as compared to the standard capsules:

Shells of standard coacervate capsules: mass ratio gelatine/gum arabic/silica=1.5/1/0.

Shells of hybrid coacervate capsules: mass ratio gelatine/gum arabic/silica=1.5/1/0.5.

Measurement of Release Upon Drying

Figure 4:
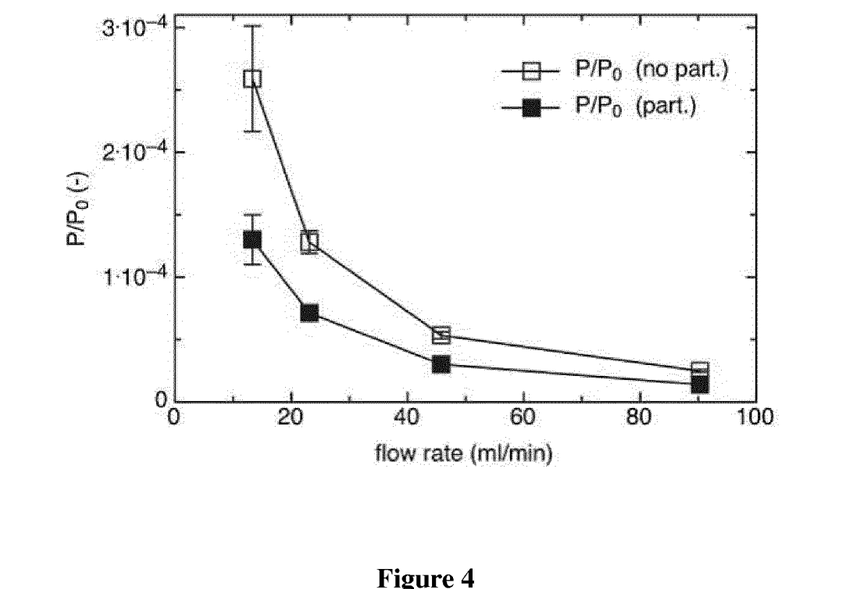
FIG. 4 shows the relative headspace concentration of an active ingredient (limonene) in relation to the flow rate for dynamic headspace measurements on classical coacervate capsules containing no particles (no part.) and hybrid coacervate capsules containing particles (part.).

In a small crystallization disk, a few drops of the capsule slurry were diluted with 1 mL of deionized water. From this suspension, average-sized single capsules were selected and transferred to a 13 mm diameter glass fiber disk (Whatman GF/B). Fifteen capsules were deposited on the disk. Water was needed for the transfer but care was taken to include only the smallest possible amount of water on the disk in order to maintain its permeability. To remove excess of water, the disk was placed on several layers of filter paper. The disk containing the dried capsules was then introduced in the flow cell and the headspace analysis (FIG. 4) was carried out as follows: The surface of the liquid was submitted to 4 different nitrogen flow rates (13.3, 23.1, 45.8 and 90.3 mL/min), at controlled temperature and saturated with water, each flow rate being applied for 10 minutes. An aliquot of 1 mL of the gas in the cell was sampled at 1 minute intervals by a CTC Analytics PAL automated sampler and injected in a GC/MS system (Agilent 6890/Agilent 5973) for analysis. The headspace measurement was performed at 32° C., and the peak area was normalized by the peak area obtained for pure limonene under static conditions at the same temperature ($P_0$). Following this protocol, each point plotted for $P/P_0$ is an average of about 10 different values. Measurements were Performed in Triplicate.

The key result is that the diffusion of limonene through the membrane of hybrid capsules is reduced by 50% to 56% as compared to standard coacervate capsules. Although the underlying mechanism for this phenomenon is unknown, it is possible that a more densely packed polymer/inorganic shell is formed upon removal of the water during drying. Ultimately, this significant result suggests a less permeable structure for the hybrid capsules after removal of the water phase in the membrane.

Example 3

Example 3a: Alternative Preparation of Hybrid Coacervate Capsules with Shells Composed of Gelatin, Gum Arabic and Silica Particles This comparative example demonstrates an unsuccessful attempt to obtain hybrid coacervate capsules when the process described in the present invention was not followed. In particular, failure to obtain complexes of polymer 1 and the solid particles led to subsequent failure of the formation of a hybrid coacervate shell, the result being classical coacervate capsules with freely suspended solid particles, which are not integrated into the capsule shell. As in Example 2, in a beaker at 50° C., 15 g of solution (A) and 10 g of solution (B) are mixed and added to 35 g of warm demineralized water under mechanical shear. The pH is adjusted to 4.5 with HCl 1M before adding 40 g of dispersion (C) to the solution, and readjusting the pH to 4.5, if necessary. 10 g of the solution (D) are then added to the mixture, under mechanical shear until the mixture reaches the desired droplet size. The solution is maintained under agitation and cooled down to room temperature. The result is a suspension of core-shell capsules exhibiting a translucent shell without particulate inclusions. Particles are located and dispersed in the continuous aqueous media. Unlike in Examples 1 and 2, no complexes of polymer 1 and particles were formed, and subsequently no particles were included in the coacervated shell of the capsules.

Example 3b: Alternative Preparation of Hybrid Coacervate Capsules with Shells Composed of Gelatin, Gum Arabic and Kaolin Particles This comparative example shows that, a hybrid coacervate phase was formed, but the crucial step of depositing this hybrid coacervate on the core material was unsuccessful such that it was not possible to encapsule the oily core liquid.

Figure 1:
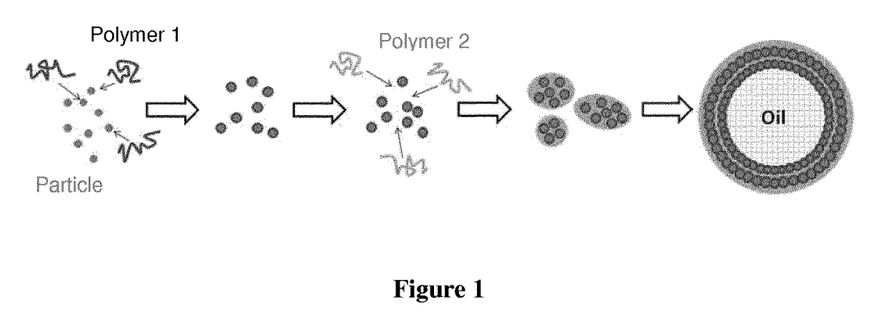
FIG. 1 shows a schematic drawing of the hybrid coacervation process of the invention.
Figure 2A:
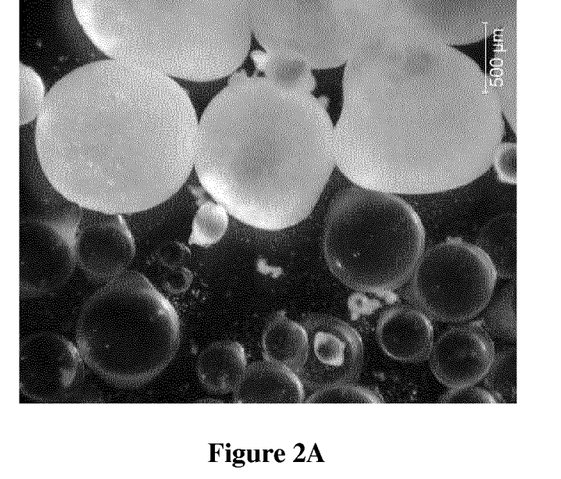
FIG. 2A shows a comparison between opaque hybrid coacervate capsules with a gelatin/gum arabic/kaolin shell (top of the figure) and classical, transparent gelatin/gum arabic coacervate capsules (bottom of the figure).
Figure 2B:
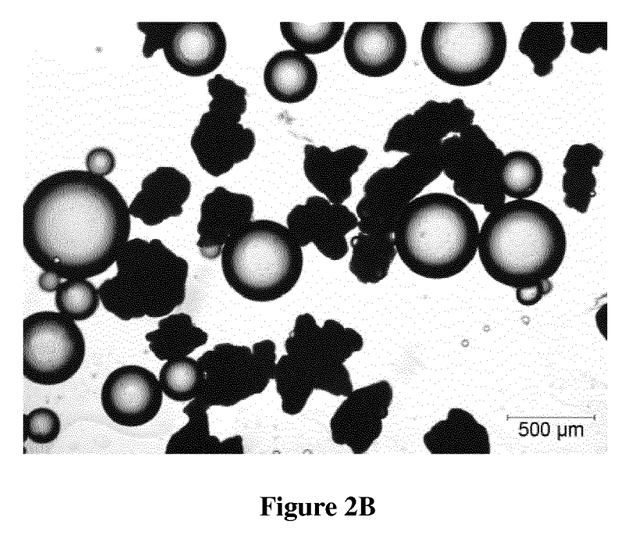
FIG. 2B shows non-encapsulated (free) oil drops alongside gelled hybrid coacervate lumps resulting from the use of a hybrid coacervate material made from (gelatin/gum arabic/kaolin) at mass ratio (1.5/1/4) that does not properly deposit onto the core material and does not form a shell.

Two different samples of the hybrid coacervate phase were prepared at a mass ratio 1.5/1/4 of ratio gelatine/gum arabic/kaolin, and the pH was adjusted to 4 and to 4.5, respectively. In both cases, a full phase separation including the polymers and the solid particles was obtained, resulting in dense nodules of irregular shape containing both polymers and the kaolin clay particles. Upon mixing with limonene oil, none of these hybrid particles was deposited on the oil drops as in the successful Examples 1 and 2 described hereinabove, and all of the hybrid coacervate gel fragments were found to remain suspended and sedimented to the bottom of the mixing beaker, as shown in FIG. 2B.

Example 3c: Encapsulation Process with Adjustment of the Viscosity of the Hybrid Coacervate Shell Material to Allow its Deposition on the Core Material In this example an encapsulation process is performed according to the procedure given in Examples 1, 2 and 3b. In addition, the viscosity of the hybrid coacervate shell is controlled by performing rheological experiments in parallel to the encapsulation experiments. The hybrid coacervates were composed of gelatin (polymer 1), gum arabic (polymer 2) and kaolin particles, and different mass ratios (polymer 1:polymer 2:particles) were investigated. The rheometer is a Physica MCR 300 (Anton Paar, Ostfildern, Germany) and a parallel plate geometry was used (diameter 50 mm, measuring gap 1 mm; the measuring fixture in contact with the sample had corrugated surfaces to avoid the problem of wall slip during the measurement). The dynamic viscosity is measured by performing a controlled shear rate ramp from high to low shear rates while controlling the temperature with the built-in Peltier temperature controller of the rheometer. Different hybrid coacervate phases were prepared as described in Examples 1, 2 and 3b, but in parallel a volume of 20 ml of each hybrid coacervate phase was withdrawn and used to measure the viscosities (in SI units of mPa*s, i.e. milliPascal*seconds). Viscosities are compared at shear rates of 100/s, 1/s and 0.01/s, which are shear rates characteristic of the mixing and deposition steps of the encapsulation process, and measurements were performed in a temperatures range between 30° C. and 55° C. The results show that for the mass ratio (1.5/1/3) and pH 4.5 as in Example 1, the viscosity measured at a shear rate of 1/s was 23,450 mPa*s at 30° C., 940 mPa*s at 37.5° C., and 390 mPa*s at 55° C. The lowest overall value of the viscosity was measured at a shear rate of 100/s at 55° C. and its value was 255 mPa*s. The highest apparent viscosity was measured at the slowest shear rate of 0.01/s at 30° C. and it was 550,000 mPa*s. It was found that the hybrid coacervate material with these properties deposits easily onto the core material during the process.

In contrast, at ratio (1.5/1/4) and pH 4 the viscosity values was increased. In particular, at a shear rate of 1/s, the viscosity was 49,320 mPa*s at 30° C., 1325 mPa*s at 37.5° C., and 405 mPa*s at 55° C. The lowest viscosity measured on the heated sample at 55° C. and with a fast shear rate of 100/s was 270 mPa*s, which is comparable in magnitude to the mass ratio described above. However, at the slow shear rate, the highest apparent viscosity was strongly increased with a very high viscosity value of 2,400,000 mPa*s at 30° C. In this case, it was found that the hybrid coacervate material was too viscous to deposit onto the core material during the process (FIG. 2B). Thus, instead of core/shell capsules, only gelled hybrid coacervate lumps and free drops of the core material were found in the resulting mixture.

These experiments therefore allows us to demarcate the limiting values of the viscosities within which a hybrid coacervate material composed of two polymers and particles can be successfully formed such that it includes a high mass fraction of particles yet is still able to deposit easily on the core material.

Example 4

Figure 5A:
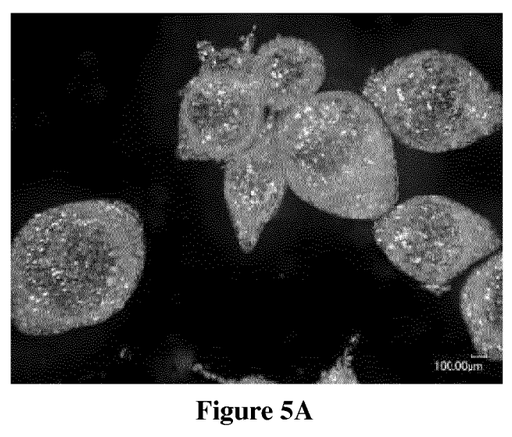
FIGS. 5A and 5B show an iridescent visual effect of hybrid coacervate capsules with shells containing gelatin/gum arabic/mica, at low (A) and high (B) magnifications.
Figure 5B:
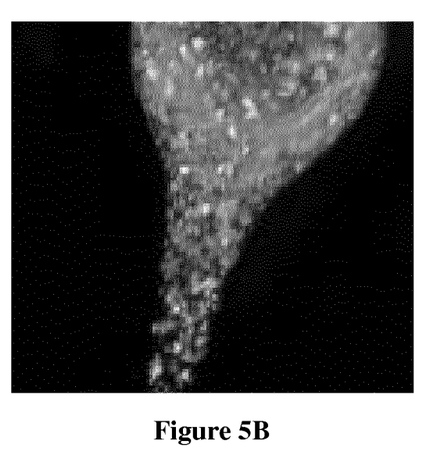

Preparation of Hybrid Coacervate Capsules with Functional Particles to Provide Desired Optical Properties or Attractive Visual Appearance This example describes the preparation of hybrid coacervate capsules with shells composed of gelatin, gum arabic and particles providing an additional functionality to the capsule, including attractive optical appearance such as opalescence, color, and iridescence (shown in FIG. 5).

Aqueous solutions of 10% wt. pork gelatine (A), 10% wt. gum arabic (B), an aqueous dispersion 10% wt. mica particles (C) and limonene oil (D) are prepared separately and maintained at 50° C. in a water bath. In a beaker at 50° C., 15 g of solution (A) are added to 70 g of warm demineralized water under mechanical shear. The pH is adjusted to 8.5 using NaOH 1M before adding 10 g of solution (C), and reducing the pH to 4.5 with HCl 1M. 10 g of solution (B) are then added to the mixture, followed by the addition of 10 g of oil (D). Mechanical shear is maintained while the solution is allowed to cool down at room temperature.

The example provided herein may be easily modified, for example, to include particles that are radiation absorbers (e.g., for UV protection).

Example 5

Preparation of Hybrid Coacervate Capsules with Iron Oxide Inclusions in the Shell This example demonstrates the formation of hybrid coacervate capsules containing $Fe_2O_3$ particles in the shell.

Aqueous solutions of 10% wt. pork gelatine (A), 10% wt. gum arabic (B), an aqueous dispersion of 10% wt. $Fe_2O_3$ (Fluka, code Fluka 44955, assay >98%) particles (C) and limonene oil (D) are prepared separately and maintained at 50° C. in a water bath. In a beaker at 50° C., 15 g of solution (A) are added to 70 g of warm demineralised water under mechanical shear. The pH is adjusted to 9.1 using NaOH 1M, before adding 5 g of solution (C), and reducing the pH to 4.5 with HCl 1M. 10 g of solution (B) are then added to the mixture, followed by the addition of 10 g of oil (D). Mechanical shear is maintained while the solution is allowed to cool down at room temperature.

Example 6

Preparation of Magnetically Responsive Hybrid Coacervate Capsules with $Fe_3O_4$ Inclusions in the Shell Capsules were made as in Example 5 but with $Fe_3O_4$ particles. The resulting capsules could be easily moved inside the vial in a contact-free manner when a simple magnet purchased in a local supermarket was held and moved against the glass wall of the container.

What is claimed is:

1. A process for preparing a hybrid coacervate capsule which comprises:
   (a) mixing a solution of a first polymer with a first dispersion of at least one type of solid particles at a temperature that is above the gelling temperature of the first polymer, wherein the first polymer adsorbs onto the at least one type of solid particles to produce a second dispersion of particle/polymer complexes;
   (b) adding a solution of a second polymer to the second dispersion, wherein the second polymer interacts with the particle/polymer complexes to form hybrid complex coacervates containing homogeneously distributed particulate inclusions, wherein the first polymer is gelatine and the second polymer is gum arabic and wherein the gelatine and gum arabic are present in a weight ratio of 1.5;
   (c) adding a core material to the hybrid complex coacervates, wherein the hybrid complex coacervates deposit as a coating layer around the core material active/solution interface to form core/shell capsules each containing the core material encapsulated by a hybrid coacervate shell; and
   (d) reducing the temperature of the core/shell capsules to a temperature that is below the gelling temperature of the first polymer;
   (e) optionally, cross-linking the hybrid coacervate shells of the capsules, wherein the hybrid coacervate shell has a dry matter composition such that the ratio of the total mass of solid particles to total mass of the first and second polymers is between 0.01 and 1.85.

2. The process according to claim 1, wherein the solution of the first polymer is mixed with the first dispersion of the at least one type of solid particles under conditions sufficient for the first polymer to adsorb readily onto the at least one type of solid particles.

3. The process according to claim 1, wherein the pH value and ionic strength of the solution of the first polymer are optimized for the formation of the particle/polymer complexes.

4. The process according to claim 1, wherein the hybrid coacervate has a suitable viscosity that allows the hybrid coacervate to deposit on the core material to form the capsule shell.

5. The process according to claim 4, wherein the viscosity of the hybrid coacervate is between 100 mPa*s and 2,500,000 mPa*s at a temperature that is between 30° C. and 70° C., and at shear rates between 0.01/s and 100/s.

6. The process according to claim 1, wherein the hybrid coacervate contains two or more types of solid particles.

7. The process according to claim 6, wherein the shell contains two or more different types of solid particles selected from the group consisting of silicon oxides and other metal oxides, silicates, silver nanoparticles, magnesium and aluminum silicates (clays), sheet silicates (mica), diatomite, perlite, vermiculite, crystals of fats, fatty acids or fatty alcohols and mixtures thereof.

8. The process according to claim 1, wherein the core comprises a solid active ingredient and/or a liquid active ingredient of an oil.

9. The process according to claim 1, wherein the particles have coverage by the first polymer of at least 0.1 molecules of polymer per square millimeter of particle surface.

10. The process according to claim 1, wherein the particles have coverage by the first polymer of at least 0.1 molecules of polymer per square millimeter of particle surface.

* * * * *